United States Patent [19]

Fellows

[11] Patent Number: 4,847,413
[45] Date of Patent: Jul. 11, 1989

[54] PROCESS FOR PREPARING 2-METHYL-2-(METHYLSULFONYL) PROPIONALDEHYDE O-(METHYLCARBAMOYL) OXIME AS A WATER-WET CAKE

[75] Inventor: Constance A. Fellows, Durham, N.C.

[73] Assignee: Rhone-Poulenc Nederland, B.V., Amstelveen, Netherlands

[21] Appl. No.: 879,694

[22] Filed: Jun. 27, 1986

[51] Int. Cl.$^4$ ............................................ C07C 131/00
[52] U.S. Cl. ...................................................... 564/255
[58] Field of Search .......................... 564/255; 514/477

[56] References Cited

U.S. PATENT DOCUMENTS

| | | | |
|---|---|---|---|
| 3,217,036 | 11/1965 | Payne | 564/268 |
| 3,217,037 | 11/1965 | Payne et al. | 564/244 |
| 3,506,698 | 4/1970 | Jelinek | 558/3 |
| 3,824,320 | 7/1974 | Buchanan | 514/477 |
| 4,097,526 | 6/1978 | Chan | 564/255 |
| 4,248,795 | 2/1981 | Chan | 568/28 |

OTHER PUBLICATIONS

Saunders, J. H. et al., *Chemical Reviews*, vol. 43 (1948) pp. 207–211.

*Primary Examiner*—James H. Reamer
*Attorney, Agent, or Firm*—Morgan & Finnegan

[57] ABSTRACT

This invention relates to a process for preparing 2-methyl-2-(methylsulfonyl) propionaldehyde O-(methylcarbamoyl) oxime as an aqueous wet cake by reacting 2-methyl-2-(methylthio) propionaldehyde oxime with methyl isocyanate in an aqueous medium to give 2-methyl-2-(methylthio) propionaldehyde O-(methylcarbamoyl) oxime which is then oxidized in an aqueous medium to give 2-methyl-2-(methylsulfonyl) propionaldehyde O-(methylcarbamoyl) oxime. This invention also relates to an aqueous wet cake composition containing 2-methyl-2-(methylsulfonyl) propionaldehyde O-(methylcarbamoyl) oxime.

27 Claims, No Drawings

PROCESS FOR PREPARING 2-METHYL-2-(METHYLSULFONYL) PROPIONALDEHYDE O-(METHYLCARBAMOYL) OXIME AS A WATER-WET CAKE

BRIEF SUMMARY OF THE INVENTION

1. Technical Field

This invention relates to a process for preparing 2-methyl-2-(methylsulfonyl) propionaldehyde O-(methylcarbamoyl) oxime (aldoxycarb) as an aqueous wet cake by reacting 2-methyl-2-(methylthio) propionaldehyde oxime (aldicarb oxime) with methyl isocyanate in an aqueous medium to give 2-methyl-2-(methylthio) propionaldehyde O-(methylcarbamoyl) oxime (aldicarb) which is then oxidized in an aqueous medium to give 2-methyl-2-(methylsulfonyl) propionaldehyde O-(methylcarbamoyl) oxime. This invention also relates to an aqueous wet cake composition containing 2-methyl-2-(methylsulfonyl) propionaldehyde O-(methylcarbamoyl) oxime.

2. Background of the Invention

The carbamoylation reaction of an oxime compound with an isocyanate compound in an organic solvent such as dichloromethane and the subsequent oxidation reaction of the resulting carbamate compound in an organic solvent is known and practiced in the art. See, for example U.S. Pat. No. 4,097,526.

U.S. Pat. No. 3,217,037 describes a process for preparing 2-hydrocarbylthio-sulfinyl and sulfonylalkanal carbamoyloximes including 2-methyl-2-(methylsulfonyl) propionaldehyde O-(methylcarbamoyl) oxime which involves reacting an oxime compound with an isocyanate compound in an inert organic solvent and thereafter oxidizing the resulting carbamate compound in an inert organic solvent. The inert organic solvents described in the patent which can be employed are those inert to isocyanates in general, i.e., those free of radicals such as hydroxy or amine radicals. Illustrative solvents described in the patent are aliphatic and aromatic hydrocarbons such as hexane, heptane, octane, benzene, toluene and the like, and ethers such as diethyl ether, ethyl propyl ether and the like.

U.S. Pat. No. 3,506,698 describes a process for preparing thiolhydroxamate carbamates which involves the reaction of thiolhydroxamate esters such as methyl thiolacetohydroxamate esters with a carbamylating agent such as isocyanic acid or its methyl ester in an aqueous medium at a temperature of between 0° C. and the boiling point of the reaction mass to obtain the corresponding thiolhydroxamate carbamates. At column 1, lines 58–60 of this patent, it is pointed out that thiolhydroxamates are not oximes.

It is therefore an object of this invention to provide a process for preparing 2-methyl-2-(methylsulfonyl) propionaldehyde O-(methylcarbamoyl) oxime by reacting 2-methyl-2-(methylthio) propionaldehyde oxime with methyl isocyanate in an aqueous medium to give 2-methyl-2-(methylthio) propionaldehyde O-(methylcarbamoyl) oxime which is then oxidized in an aqueous medium to give 2-methyl-2-(methylsulfonyl) propionaldehyde O-(methylcarbamoyl) oxime, and thereby eliminating the need for organic solvents. It is another object of this invention to provide a water-wet cake composition containing 2-methyl-2-(methylsulfonyl) propionaldehyde O-(methylcarbamoyl) oxime.

DISCLOSURE OF THE INVENTION

This invention relates to a process for preparing 2-methyl-2-(methylsulfonyl) propionaldehyde O-(methylcarbamoyl) oxime which comprises (i) reacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime and (ii) reacting 2-methyl-2-(methylthio) propionaldehyde O-(methylcarbamoyl) oxime with a mixture of hydrogen peroxide and a carboxylic acid in the presence of an aqueous medium and a catalytically effective amount of a mineral or organic sulfonic acid for a period sufficient to form 2-methyl-2-(methylsulfonyl) propionaldehyde O-(methylcarbamoyl) oxime. This invention further relates to a water-wet cake composition containing 2-methyl-2-(methylsulfonyl) propionaldehyde O-(methylcarbamoyl) oxime. As used herein, step (i) is referred to as the carbamoylation step and step (ii) is referred to as the oxidation step.

DETAILED DESCRIPTION

As stated above, the process for this invention is carried out in the presence of water rather than an organic solvent. This is a significant discovery for several reasons. The use of water provides for increased safety in comparison with certain organic solvents which may exhibit toxic properties or pose other health and safety hazards. In addition, the use of water avoids any adverse environmental aspects such as air and water pollution which may be associated with certain organic solvents. Further, in comparison with certain organic solvents, the use of water is economically advantageous in that is inexpensive and no recycle is necessary.

The process of this invention can be carried out by contacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime which is reacted with a mixture of hydrogen peroxide and a carboxylic acid in the presence of an aqueous medium and a catalyst, i.e., mineral or organic sulfonic acid, to give 2-methyl-2-(methylsulfonyl) propionaldehyde O-(methylcarbamoyl) oxime as a solid in an aqueous slurry which is then filtered to give a water-wet cake.

2-Methyl-2-(methylthio) propionaldehyde oxime is a known material which can be prepared according to the procedure described in U.S. Pat. No. 3,217,036. Methyl isocyanate is a known material which can be prepared by conventional methods. 2-Methyl-2-(methylthio) propionaldehyde O-(methylcarbamoyl) oxime is a known material which is the active ingredient in various TEMIK ® brand aldicarb pesticides available from Union Carbide Agricultural Products Company, Inc., Research Triangle Park, N.C. Hydrogen peroxide, the carboxylic acids and the mineral and organic sulfonic acid catalysts are conventional materials known in the art. 2-Methyl-2-(methylsulfonyl) propionaldehyde O-(methylcarbamoyl) oxime is a known material which is the active ingredient in various STANDAK ® brand aldoxycarb pesticides available from Union Carbide Agricultural Products Company, Inc., Research Triangle Park, N.C.

The amount of water used in the process of this invention is not narrowly critical and can vary over a wide range. In general, the molar ratio of 2-methyl-2-

(methylthio) propionaldehyde oxime to water can range from about 1:1 or less to about 1:50 or greater, preferably from about 1:10 to about 1:40. The amount of water used in the process of this invention is in general influenced primarily by reaction equipment including heat removal capability and solids handling capability.

The amount of 2-methyl-2-(methylthio) propionaldehyde oxime and methyl isocyanate used in the carbamoylation step of the process of this invention can vary over a wide range. In general, the molar ratio of methyl isocyanate to 2-methyl-2-(methylthio) propionaldehyde oxime can range from about 0.25:1 to about 2:1. Preferably, an equimolar amount or slight excess of methyl isocyanate is employed to ensure that 2-methyl-2-(methylthio) propionaldehyde oxime is completely reacted.

A catalyst can optionally be used in the carbamoylation step of the process of this invention. Suitable catalysts include a tertiary amine or an organotin catalyst. Other suitable catalysts include alkali metal and alkaline earth metal oxides, carbonates, bicarbonates or basic ion exchangers and carboxylic acid derivative salts. Illustrative tertiary amine catalysts include, for example, triethylamine, trimethylamine and the like. Illustrative organotin catalysts include, for example, dibutyltin diacetate, dibutyltin dichloride, dibutyltin dimethoxide, dibutyltin dilaurate, dibutyltin maleate, dibutyltin di-2-ethylhexenoate, stannous octanoate, stannous oleate and the like. Such catalysts are conventional materials known in the art.

The amount of catalyst which can be used in the carbamoylation step of the process of this invention is a catalytically effective amount and can vary over a wide range. Generally, the amount of catalyst employed can range from about 0.01 weight percent to about 1.0 weight percent or higher based on the total weight of methyl isocyanate and 2-methyl-2-(methylthio) propionaldehyde oxime.

The reaction temperature for the carbamoylation step is not critical and can be varied over a wide range. The carbamoylation step of process of this invention is normally conducted at a temperature in the range of from about 0° C. to about 30° C. Preferably from about 5° C. to about 25° C. The reaction temperature is in general limited primarily by physical constraints such as vaporization or freezing of the reactants or other ingredients. At temperatures below about 0° C., 2-methyl-2-(methylthio) propionaldehyde oxime tends to freeze out while at temperatures in excess of about 30° C. the reaction of methyliisocyanate with water is favored over the reaction of methyl isocyanate with 2-methyl-2-(methylthio) propionaldehyde oxime. The reaction of methyl isocyanate with 2-methyl-2-(methylthio) propionaldehyde oxime proceeds significantly faster than the reaction of methyl isocyanate with water at temperatures from about 0° C. to about 30° C.

Reaction pressures for the carbamoylation step are not critical. The carbamoylation step of the process of this invention can be conducted at either subatmospheric, atmospheric or superatmospheric pressure. For convenience, the reaction is usually conducted at atmospheric or autogenous pressure.

The reaction time period for the carbamoylation step is not narrowly critical and can vary from second(s) or instantaneously to as long as several hours. The carbamoylation step of the process of this invention is conducted over a period of time sufficient to produce 2-methyl-2-(methylthio) propionaldehyde O-(methylcarbamoyl) oxime. Generally, when operating in the preferred temperature range, reaction times of from about one-half hour or less to about 4 hours are sufficient to complete the reaction of methyl isocyanate with 2-methyl-2-(methylthio) propionaldehyde oxime. Reaction time is influenced by the reaction temperature, the concentration and choice of catalyst and other factors known to those skilled in the art.

The carbamoylation step of the process of this invention can be conducted by mixing 2-methyl-2-(methylthio) propionaldehyde oxime with water at a preferred temperature of from about 0° C. to about 30° C. after which a catalyst is optionally added to the mixture. While maintaining the reaction temperature between about 0° C. and 30° C., methyl isocyanate is added with vigorous stirring over a sufficient period of time to provide for substantially complete conversion of 2-methyl-2-(methylthio) propionaldehyde oxime to 2-methyl-2-(methylthio) propionaldehyde O-(methylcarbamoyl) oxime. The carbamoylation step of the process of this invention can provide 2-methyl-2-(methylthio) propionaldehyde O-(methylcarbamoyl) oxime on a yield basis in excess of 90 percent based on the weight of 2-methyl-2-(methylthio) propionaldehyde oxime.

The methyl isocyanate addition period can range from seconds to hours or longer, and can occur over one, two or even more separate addition periods, i.e., batchwise, continuously or intermittently introduced into the reaction mixture. Generally, the methyl isocyanate addition period can range from about one-half hour or less to about 2 hours or longer depending upon the amount of 2-methyl-2-(methylthio) propionaldehyde oxime and catalyst employed in the process and the ability to control the reaction temperature. The stirring period can also range from seconds to hours or longer and can be approximately co-extensive with the methyl isocyanate addition period. However, the stirring period is generally longer than the methyl isocyanate addition period in order to effect substantially complete conversion of 2-methyl-2-(methylthio) propionaldehyde oxime to 2-methyl-2-(methylthio) propionaldehyde O-(methylcarbamoyl) oxime.

Other ingredients can optionally be employed in the carbamoylation step of the process of this invention. An organic or inorganic acid can be used to quench the reaction (tie up the catalyst and raise the reaction PH to about 4 or 5). Suitable organic and inorganic acids include phosphoric acid, hydrochloric acid sulfuric acid, acetic acid and the like. The amount of acid which can be employed is not narrowly critical and is dependent upon the amount of catalyst and reactants used in the process. The amount of acid can range from 0.0001 weight percent or less to about 1.0 weight percent or greater based on the weight of the entire reaction mass.

The carboxylic acids useful in the oxidation step of the process of this invention are known in the art. Illustrative of carboxylic acids useful in the oxidation step of the process of this invention are benzoic acid, p-chlorophenoxyacetic acid acetic acid, butanoic acid, heptanoic acid, formic acid, p-methoxybenzoic acid, toluic acid, valeric acid, propionic acid, B-naphthoic acid, 4-(1 naphthyl)-4-butanoic acid, 3-(2-naphthyl)butyric acid or the like. In general, at least one mole of carboxylic acid per equivalent of the divalent sulfide functional unit present in 2-methyl-2-(methylthio) propionaldehyde O-(methylcarbamoyl) oxime should be employed in the oxidation step. The preferred amount of carboxylic acid employed is from about 1 to about 4 moles of acid per equivalent of the divalent sulfide functional unit. The particularly preferred amount of carboxylic acid employed is from about 1.5 to about 2.0 moles per mole of the divalent sulfide functional unit.

In order to achieve a satisfactory conversion of 2-methyl-2-(methylthio) propionaldehyde O-(methylcarbamoyl) oxime to 2-methyl-2-(methylsulfonyl) propionaldehyde O-(methylcarbamoyl) oxime, an excess of hydrogen peroxide should be employed. The preferred amount of hydrogen peroxide is from about 2 to about 5 moles of hydrogen peroxide per equivalent of the divalent sulfide functional unit. The particularly preferred amount of hydrogen peroxide is from about 2.3 to about 2.0 moles per mole of the divalent sulfide functional unit.

The oxidation step of the process of this invention is conducted in the presence of an acid catalyst. In general, any conventional mineral acid or organic sulfonic acid may be used. Illustrative of suitable mineral acids that can be employed in the oxidation step of the process of this invention are phosphoric acid, nitric acid, sulfuric acid, hydrochloric acid, boric acid, perchloric acid, hypochloric acid and the like. Illustrative of useful organic sulfonic acids are benzenesulfonic acid, p-toluenesulfonic acid, p-nitrobenzenesulfonic acid, 2-naphthalenesulfonic acid and the like. The acid catalyst employed in the oxidation step can be initially introduced into the reaction zone batchwise or it may be continuously or intermittently introduced in such zone during the oxidation step of the process.

The quantity of acid catalyst employed in the oxidation step of the process of this invention is a catalytically effective amount and can be varied over a wide range. In general, the reaction proceeds satisfactory when employing as little as about 0.01 weight percent of the acid catalyst based on the quantity of the reactants. The upper concentration limit can be quite high, as for example about 10.0 weight percent, and higher. In the preferred embodiment of this process, an acid catalyst concentration of from about 0.10 to about 7.0 weight percent based on quantity of the reactants is useful.

The reaction temperature for the oxidation step can be varied over a wide range. The process is normally conducted at a temperature in the range of from about 0° C. and upwards to approximately 75° C. Preferred reaction temperatures are from about 25° C. to about 60° C. At temperatures below 25° C., the rate of reaction becomes markedly slower, while at temperatures above about 60° C., product degradation may occur.

Reaction pressures for the oxidation step are not critical. The oxidation step of the process of this invention can be conducted at either subatmospheric, atmospheric or superatmospheric pressure. For convenience, the reaction is usually conducted at atmospheric or autogenous pressure.

The oxidation step of the process of this invention can be effected over a period of time sufficient to produce 2-methyl-2-(methylsulfonyl) propionaldehyde O-(methylcarbamoyl) oxime. In general, reaction times can vary from a few minutes to approximately 24 hours or longer. In most instances, when employing preferred reaction conditions, reaction times will be found to vary from about 2 hours to about 4 hours. Reaction time for the oxidation step is influenced by the reaction temperature, the concentration and choice of acid catalyst and other factors known to those skilled in the art.

The oxidation step of the process of this invention can be conducted by treating 2-methyl-2-(methylthio) propionaldehyde O-(methylcarbamoyl) oxime with an aqueous mixture of hydrogen peroxide, a carboxylic acid, and a catalytic amount of a mineral acid or an organic sulfonic acid in the presence of water. The manner and order in which the reaction components in the oxidation step are mixed is not critical. In general, 2-methyl-2-(methylthio) propionaldehyde O-(methylcarbamoyl) oxime, the carboxylic acid and water are placed in a suitable reaction vessel and hydrogen peroxide and the acid catalysts are added in consecutive order, preferably with moderate agitation and the reaction mass heated to the desired temperature.

Antifoaming agents and surfactants can optionally be employed in the process of this invention. Such antifoaming agents and surfactants are conventional materials known in the art. Suitable antifoaming agents include, for example, SAG 10 and SAG 30 which are available from Union Carbide Corporation, Danbury, Conn. and Q-132, which is available from SWS Silicones Corporation, Adrian, Mich. Suitable surfactants include conventional ionic and nonionic materials such as Tergitol 15-S7 available from Union Carbide Corporation, Danbury, Conn. and Pluronic L-61 and L-101 available from BASF. The amount of antifoaming agent and surfactant employed in the process of this invention can range from about 0.0001 weight percent or less to about 1.0 weight percent (based on the weight of the entire reaction mass) or greater for each ingredient.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure. Means to introduce and/or adjust the quantity of reactants or ingredients introduced, either intermittently or continuously into the reaction zone during the course of the reaction can be conveniently utilized in the process especially to maintain the desired molar ratio of the reactants.

The process is preferably conducted in either glass lined, stainless steel or similar type reaction equipment. The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reaction mixtures can be employed. Mixing by vibration, shaking, stirring, rotation, oscillation, ultrasonic vibration or the like are all illustrative of the types of agitation means contemplated. Such means are available and well known to those skilled in the art.

As stated above, a water-wet cake product is prepared by the process of this invention. The water-wet cake product generally contains from about 70 weight percent to about 95 weight percent or greater of 2-methyl-2-(methylsulfonyl) propionaldehyde O-(methylcarbamoyl) oxime, less than about 0.1 weight percent to about 15 weight percent of 2-methyl-2-(methylsulfonyl) propionaldehyde O-(methylcarbamoyl) oxime and from about 5 weight percent or less to about 30 weight percent of water (weight percent based on the total weight of the product). Amounts of water greater than about 30 weight percent tend to provide a slurry product rather than a water-wet cake product. Other ingredients such as an organic or inorganic acid, an antifoaming agent and a surfactant as described above and certain impurities, e.g., methacrolein oxime carbamate, can be present in the water-wet cake product in minor amounts, e.g., individual amounts from about 0.0001 weight percent or less to about 1 weight percent.

The water-wet cake product prepared by the process of this invention is useful in formulating various STANDAK ® brand aldoxycarb pesticides available from Union Carbide Agricultural Products Company, Inc., Research Triangle Park, N.C.

The following examples are illustrative of the process of this invention.

EXAMPLE 1

Into a one liter glass resin kettle equipped with an air-driven stirrer, a pressure-equalizing dropping funnel with Teflon ® tube for subsurface addition, a thermometer and a dry ice/acetone cooled condenser was added 66.5 grams (0.50 mole) of 2-methyl-2-(methylthio) propionaldehyde oxime (aldicarb oxime) and 112 milliliters of water. After the mixture was cooled to a temperature of 15° C. with a water/salt/ice bath, 0.2 grams (0.002 mole) of triethylamine was added to the kettle under a nitrogen atmosphere. An amount of methyl isocyanate slightly in excess of stoichiometric (32.4 milliliters, 0.55 mole) was then added subsurface over a period of 20 minutes with vigorous stirring. The reaction temperature rose to 28° C. -30° C. The mixture was stirred at ambient temperature for a period of 30 minutes after which 1.0 gram of phosphoric acid in 0.5 grams of water was added dropwise. To this continuously stirred mixture was added 52.3 grams (1.0 mole) of formic acid and 80 milliliters of water at a temperature of 24° C. A 30 percent solution of hydrogen peroxide in water (127 grams) was then added dropwise over a period of 30 minutes with the temperature maintained at 40° C.–60° C. after which 10.4 grams of concentrated sulfuric acid was added. The mixture was stirred for a period of 45 minutes at a temperature of 48° C. and then chilled overnight at a temperature of 0° C.–5° C. The resulting solid product was filtered off on a sintered glass funnel to give two crops of crystals having a combined weight of 68.9 grams and having a melting point of 137° C.–137.5° C. High pressure liquid chromatographic analysis (internal standard) indicated the following: 77 percent 2-methyl-2-(methylsulfonyl) propionaldehyde O-(methylcarbamoyl) oxime (aldoxycarb) and 13.8 percent 2-methyl-2-(methylsulfinyl) propionaldehyde O-(methylcarbamoyl) oxime; 9.2 percent water content was determined by Karl Fischer titration.

I claim:

1. A process for preparing 2-methyl-2-(methylsulfonyl) propionaldehyde O-(methylcarbamoyl) oxime which comprises (i) reacting 2-methyl-2-(methylthio) propionaldehyde oxime with methyl isocyanate in the presence of an agueous medium for a period sufficient to form 2-methyl-2-(methylthio) propionaldehyde O-(methylcarbamoyl) oxime and (ii) reacting 2-methyl-2-(methylthio) propionaldehyde O-(methylcarbamoyl) oxime with a mixture of hydrogen peroxide and a carboxylic acid in the presence of an aqueous medium and a catalytically effective amount of a mineral or organic sulfonic acid for a period sufficient to form 2-methyl-2-(methylsulfonyl) propionaldehyde O-(methylcarbamoyl) oxime.

2. The process of claim 1 in which the molar ratio of 2-methyl-2-(methylthio) propionaldehyde oxime to water is from about 1:1 to about 1:50.

3. The process of claim 1 in which the molar ratio of methyl isocyanate to 2-methyl-2-(methylthio) propionaldehyde oxime in step (i) is from about 0.25:1 to about 2:1.

4. The process of claim 1 in which a catalyst is added to the reaction in step (i).

5. The process of claim 4 in which the catalyst in step (i) is a tertiary amine or organotin catalyst.

6. The process of claim 4 in which the catalyst in step (i) is triethylamine or trimethylamine.

7. The process of claim 4 in which the catalyst in step (i) is present in an amount of from about 0.01 weight percent to about 1.0 weight percent based on the weight of methyl isocyanate and 2-methyl-2-(methylthio) propionaldehyde oxime.

8. The process of claim 1 in which the reaction temperature in step (i) is from about 0° C. to about 30° C.

9. The process of claim 1 in which the aqueous medium in step (i) is water.

10. The process of claim 1 in which the reaction period in step (i) is from about 1 second or instantaneous to about 10 hours.

11. The process of claim 1 in which an organic or inorganic acid is added to the reaction in step (i) .

12. The process of claim 11 in which the acid is phosphoric acid.

13. The process of claim 11 in which the acid is added in an amount sufficient to quench the reaction in step (i).

14. The process of claim 1 in which the carboxylic acid in step (ii) is formic acid.

15. The process of claim 1 in which the carboxylic acid in step (ii) is present in an amount of from about 1 to about 4 moles of the acid per equivalent of the divalent sulfide functional unit present in 2-methyl-2-(methylthio) propionaldehyde O-(methylcarbamoyl) oxime.

16. The process of claim 1 in which hydrogen peroxide in step (ii) is present in an amount of from about 2 to about 5 moles of hydrogen peroxide per equivalent of the divalent sulfide functional unit present in 2-methyl-2-(methylthio) propionaldehyde O-(methylcarbamoyl) oxime.

17. The process of claim 1 in which the mineral or organic sulfonic acid catalyst in step (ii) is sulfuric acid.

18. The process of claim 1 in which the mineral or organic sulfonic acid catalyst in step (ii) is present in an amount of from about 0.01 weight percent to about 10.0 weight percent based on the weight of the reaction mass.

19. The process of claim 1 in which the reaction temperature in step (ii) is from about 0° C. to about 75° C.

20. The process of claim 1 in which the aqueous medium in step (ii) is water.

21. The process of claim 1 in which the reaction period in step (ii) is from about 1 minute to about 10 hours.

22. The process of claim 1 in which an antifoaming agent is added to the reaction.

23. The process of claim 22 in which the antifoaming agent is added in an amount of from about 0.0001 weight percent to about 1.0 weight percent based on the total weight of the reaction mass.

24. The process of claim 1 in which a surfactant is added to the reaction.

25. The process of claim 24 in which the surfactant is added in an amount of from about 0.0001 weight percent to about 1.0 weight percent based on the total weight of the reaction mass.

26. The process of claim 1 in which 2-methyl-2-(methylsulfonyl) propionaldehyde O-(methylcarbamoyl) oxime is recovered by filtration.

27. A process for preparing 2-methyl-2-(methylsulfonyl) propionaldehyde O-(methylcarbamoyl) oxime which comprises (i) reacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime and (ii) reacting 2-methyl-2-(methylthio) propionaldehyde O-(methylcarbamoyl) oxime with a mixture of hydrogen peroxide and a carboxylic acid in the presence of a substantially aqueous medium and a catalytically effective amount of a mineral or organic sulfonic acid for a period sufficient to form 2-methyl-2-(methylsulfonyl) propionaldehyde O-(methylcarbamoyl) oxime.

* * * * *